United States Patent
Ben Abdelaziz et al.

(10) Patent No.: US 11,834,053 B2
(45) Date of Patent: Dec. 5, 2023

(54) ELECTRONIC DEVICE AND METHOD FOR MONITORING THE BEHAVIOR OF A DRIVER WITH DRIVING A VEHICLE, RELATED ELECTRONIC SUPERVISION SYSTEM AND COMPUTER-READABLE MEDIUM

(71) Applicant: FAURECIA INTERIEUR INDUSTRIE, Nanterre (FR)

(72) Inventors: Omar Ben Abdelaziz, Tille (FR); Nour Besbes, Maisons Laffitte (FR)

(73) Assignee: FAURECIA INTERIEUR INDUSTRIE, Nanterre (FR)

( * ) Notice: Subject to any disclaimer, the term of this patent is extended or adjusted under 35 U.S.C. 154(b) by 0 days.

(21) Appl. No.: 17/711,746

(22) Filed: Apr. 1, 2022

(65) Prior Publication Data

US 2022/0315013 A1 Oct. 6, 2022

(30) Foreign Application Priority Data

Apr. 1, 2021 (FR) ................................ FR 21 03402

(51) Int. Cl.
*B60W 40/09* (2012.01)
*B60Q 3/70* (2017.01)
(Continued)

(52) U.S. Cl.
CPC .............. *B60W 40/09* (2013.01); *B60Q 3/70* (2017.02); *B60W 50/14* (2013.01); (Continued)

(58) Field of Classification Search
CPC ................ B60W 40/09; B60W 50/14; B60W 2040/0818; B60W 2050/146; B60W 2420/42; B60W 2540/225; B60W 2540/229; B60Q 3/70; G06V 20/597; G06V 40/10

See application file for complete search history.

(56) References Cited

U.S. PATENT DOCUMENTS 8,487,775 B2 7/2013 Victor
10,476,488 B2 11/2019 Shi et al.
(Continued)

OTHER PUBLICATIONS

French Search Report corresponding to French Application No. FR 2103402, dated Nov. 29, 2021, 2 pages.

*Primary Examiner* — Mohamed Barakat
(74) *Attorney, Agent, or Firm* — REISING ETHINGTON P.C.

(57) ABSTRACT

An electronic device for monitoring the behavior of a driver is adapted to be carried on board a vehicle and to be connected to a sensor of at least one image of the driver's head and to at least one light source positioned within a passenger compartment of the vehicle. The monitoring device includes: a module for detecting abnormal behavior of the driver, from at least one image of his head acquired by the image sensor(s); a stimulation module configured, following the detection of said abnormal behavior, to command the emission of at least one light signal by switching on at least one respective light source according to an initial stimulation level; and a module for evaluating a reaction of the driver, on the basis of at least one image of the driver's head following the emission of the light signal(s).

19 Claims, 3 Drawing Sheets

(51) Int. Cl.
*G06V 40/10* (2022.01)
*G06V 20/59* (2022.01)
*B60W 50/14* (2020.01)
*B60W 40/08* (2012.01)

(52) U.S. Cl.
CPC .......... *G06V 20/597* (2022.01); *G06V 40/10* (2022.01); *B60W 2040/0818* (2013.01); *B60W 2050/146* (2013.01); *B60W 2420/42* (2013.01); *B60W 2540/225* (2020.02); *B60W 2540/229* (2020.02)

(56) References Cited

U.S. PATENT DOCUMENTS

| | | | |
|---|---|---|---|
| 11,188,074 B1* | 11/2021 | Benavidez | G05D 1/0044 |
| 2007/0132950 A1 | 6/2007 | Victor et al. | |
| 2008/0231461 A1 | 9/2008 | Sanchez et al. | |
| 2010/0033333 A1 | 2/2010 | Victor et al. | |
| 2014/0139341 A1* | 5/2014 | Green | A61B 5/18 |
| | | | 340/576 |
| 2014/0276090 A1* | 9/2014 | Breed | A61B 5/1455 |
| | | | 600/473 |
| 2017/0174082 A1* | 6/2017 | Brandt | G02B 27/01 |
| 2017/0336678 A1* | 11/2017 | Wu | G02F 1/133512 |
| 2018/0118109 A1* | 5/2018 | Fujisawa | G02B 27/01 |
| 2019/0236386 A1 | 8/2019 | Yu et al. | |
| 2020/0307619 A1* | 10/2020 | Huang | G08G 1/163 |

\* cited by examiner

ELECTRONIC DEVICE AND METHOD FOR MONITORING THE BEHAVIOR OF A DRIVER WITH DRIVING A VEHICLE, RELATED ELECTRONIC SUPERVISION SYSTEM AND COMPUTER-READABLE MEDIUM

CROSS-REFERENCE TO RELATED APPLICATIONS

This application is a U.S. non-provisional application claiming the benefit of French Application No. 21 03402, filed on Apr. 1, 2021, which is incorporated herein by reference in its entirety.

TECHNICAL FIELD

The present invention relates to an electronic monitoring device for monitoring the behavior of a driver while driving a vehicle, the device being adapted to be carried on board the vehicle and to be connected to a sensor of at least one image of the driver's head and to at least one light source positioned within a passenger compartment of the vehicle.

The invention also relates to an electronic supervision system for supervising a driver of a vehicle, the system being adapted to be carried on board the vehicle and comprising an image sensor(s) configured to acquire at least one image of the driver's head; at least one light source configured to be positioned within a passenger compartment of the vehicle; and such an electronic monitoring device for monitoring the driver's behavior while driving the vehicle, the device being connected to the image sensor(s) and the at least one light source.

The invention also relates to a vehicle, in particular a motor vehicle, comprising such an electronic supervision system.

The invention also relates to a monitoring method for monitoring a driver's behavior while driving a vehicle, implemented by such an electronic monitoring device; and to a non-transitory computer-readable medium including a computer program comprising software instructions which, when executed by a computer, implement such a monitoring method.

The invention relates to the field of vehicles, especially automobiles, and in particular to the prevention of accidents involving such vehicles.

The invention then relates to the field of vehicle driver supervision, in particular to the field of monitoring driver behavior when driving a respective vehicle. The invention is particularly concerned with the field of monitoring cognitive driver distraction.

BACKGROUND

A method for analyzing data based on a driver's physiological orientation is known from U.S. Pat. No. 8,487,775 B2. The data is descriptive of the driver's gaze orientation while driving, and criteria defining a place of interest for the driver are determined. On the basis of the determined criteria, instances of gaze orientation are then classified as being either in the right direction or in the wrong direction. Instances classified in this way can then be used for further analysis, usually in relation to periods of high driver workload, not driver drowsiness. Classified instances are converted into one of two binary values representing whether the classified instance is in the right or wrong direction. The use of such a binary value then makes data processing and analysis faster and more efficient.

U.S. Pat. No. 10,476,488 B2 relates to a method of analyzing a driver's attentional margin, and preventing inattentive and unsafe driving by the driver. The method is implemented by a computing device and comprises receiving characteristics from a camera facing the driver and another camera facing the road; receiving characteristics reflecting the driver's behavior, including head and eye movement, speech and gestures; receiving vehicle telemetry characteristics; further receiving characteristics reflecting the driver's biometrics; and then determining the driver's attention and emotional state via a decision engine receiving information representing each of the above characteristics. The purpose of determining this driver attention and emotional state is to evaluate the risks associated with the moving vehicle, as well as the driver's ability to cope with such risks.

US 2019/0236386 A1 relates to a computer-implemented method for detecting driver distraction while driving. The method comprises determining a primary preview region, also referred to as a PPR, in a representation of an environment; determining a viewpoint of the driver, based on a sequence of images of the driver; detecting whether the viewpoint of the driver is outside the PPR. This method then further comprises decreasing a driver's attention level for the PPR if the driver's viewpoint is detected outside the PPR; and then generating an alert based on the driver's attention level for the PPR.

However, with such methods, the monitoring of the driver's behavior while driving the vehicle is not optimal.

SUMMARY

An object of the invention is then to provide an electronic monitoring device, and a related monitoring method, for monitoring a driver's behavior when driving a vehicle, enabling the monitoring of said behavior to be improved, and thus reducing the risks of vehicle accidents.

To that end, the present invention relates to an electronic monitoring device for monitoring the behavior of a driver while driving a vehicle, the device being adapted to be carried on board the vehicle and to be connected to a sensor of at least one image of the driver's head and to at least one light source positioned within a passenger compartment of the vehicle, the device comprising:
- a detection module configured to detect abnormal behavior of the driver, from at least one image of the driver's head acquired by the image sensor(s);
- a stimulation module configured to, following the detection of said abnormal behavior, command an emission of at least one light signal by switching on at least one respective light source according to a predefined initial stimulation level;
- an evaluation module configured to evaluate a reaction of the driver, based on at least one image of the driver's head following the emission of the at least one light signal, acquired by the image sensor(s).

The detection module makes it possible to detect abnormal behavior of the driver, from one or more images of the driver's head acquired by the image sensor(s), such abnormal behavior corresponding, for example, to an absence of movement of the driver's eyes for a duration exceeding a first predefined threshold. If such abnormal behavior is detected, the stimulation module can then send at least one stimulus to the driver in the form of at least one light signal emitted by at least one respective light source depending on the initial stimulation level, to elicit a reaction from the driver. The evaluation module can then evaluate a reaction of the driver to the at least one stimulus, i.e. to the emission of at least one light signal. This reaction evaluation is typically displayed on a display screen to the driver to make the driver aware of their possible cognitive distraction and to encourage the driver to concentrate more on driving to reduce the risk of a driving accident.

For example, the driver's reaction is evaluated according to a reaction time of the driver since the emission of the at least one light signal, i.e. according to the time taken by the driver to react following the emission of the stimulus.

In addition, the monitoring device can also evaluate a useful field of view of the driver, also known as UFOV (Useful Field Of View), by commanding the emission of light signals from different positions within the vehicle interior, the useful field of view of the driver then depending on the position(s) of the light signals that have caused a sufficient reaction from the driver.

The subsequent action(s) taken by the monitoring device then typically depend on the reaction of the driver evaluated by the evaluation module. For example, if the driver's reaction is evaluated as sufficient, then no further stimulation is required, and the monitoring device then looks for any new abnormal behavior of the driver via its detection module.

However, if the driver's response has been evaluated as insufficient, then the monitoring device seeks to further stimulate the driver, and the stimulation module is preferably further configured to command a further emission of at least one light signal according to a next level of stimulation, distinct from the initial level of stimulation. The next stimulation level is, for example, higher than the initial stimulation level.

As a further optional complement, the device further comprises a module for generating an alert, such as an audible alert, if N insufficient reactions of the driver are successively evaluated, N being an integer of a predefined value, typically of a value greater than or equal to 3, preferably still equal to 3. The generation module then provides an additional warning if the driver has not reacted sufficiently to the N successive light stimuli.

According to other advantageous aspects of the invention, the electronic monitoring device comprises one or more of the following features, taken in isolation or in any technically possible combination:
  the stimulation module is further configured, following the evaluation of an insufficient reaction of the driver, to command a new emission of at least one light signal according to a next stimulation level, distinct from the initial stimulation level;
  each stimulation level depends on at least one parameter from the group consisting of: a position of the respective light signal, a color of the respective light signal, a brightness of the respective light signal, and a frequency of the respective light signal;
  the stimulation module is configured, following the detection of said abnormal behavior, to command the emission of several light signals at the same time, by switching on M light sources located at distinct positions inside the passenger compartment;
  the M light sources are preferably arranged on either side of a driving position of the vehicle; and optionally, M being equal to 2;
  the detected abnormal behavior is an absence of eye movement by the driver for a duration exceeding a first predefined threshold;
  the evaluation module is configured to evaluate the driver's reaction according to a reaction time of the driver since the at least one light signal was emitted;
  the reaction is evaluated as insufficient if the driver's reaction time is greater than a second predefined threshold;
  the second threshold preferably being between 2 and 3 seconds, and more preferably substantially equal to 2.5 seconds;
  the evaluation module is further configured to estimate a level of driver distraction based on a reaction time of the driver since the at least one light signal was emitted, and for a given stimulation level, the higher the reaction time, the higher the estimated distraction level;
  the device further comprises a generation module configured to generate an alert if N insufficient driver reactions are successively evaluated, where N is a predefined integer;
  N being preferably greater than or equal to 3, and even more preferably equal to 3;
  the device further comprises a display module configured to display, on a display screen disposed inside a passenger compartment of the vehicle opposite a seat for the driver, information relating to the driver's behavior;
  the display module preferably being configured to display information relating to the driver's reaction evaluated by the evaluation module and/or information relating to a level of driver distraction evaluated by the evaluation module; and
  the stimulation module is configured to command a new emission of at least one light signal only after the expiry of a predefined duration since the previous emission of at least one light signal.

The invention also relates to an electronic supervision system for supervising a driver of a vehicle, the system being adapted to be carried on board the vehicle and comprising:
  an image sensor(s) configured to acquire at least one image of the driver's head;
  at least one light source configured to be positioned within a passenger compartment of the vehicle; and
  an electronic monitoring device for monitoring the behavior of the driver while driving the vehicle, the device being connected to the image sensor(s) and to the at least one light source; the electronic monitoring device being as defined above.

The invention also relates to a vehicle, in particular a motor vehicle, comprising an electronic supervision system for supervising a driver of the vehicle, the electronic supervision system being as defined above.

The invention further relates to a monitoring method for monitoring the behavior of a driver while driving a vehicle, the method being implemented by an electronic monitoring device adapted to be carried on board the vehicle and to be connected to a sensor of at least one image of the driver's head and to at least one light source positioned within a passenger compartment of the vehicle, the method comprising the following steps:
  detecting abnormal behavior of the driver, from at least one image of the driver's head acquired by the image sensor(s);
  following the detection of said abnormal behavior, commanding an emission of at least one light signal by switching on at least one respective light source according to a predefined initial stimulation level;

evaluating a reaction of the driver, based on at least one image of the driver's head following the emission of the at least one light signal, acquired by the image sensor(s).

The invention also relates to a non-transitory, computer-readable medium including a computer program comprising software instructions, which, when carried out by a computer, implement a monitoring method as defined above.

BRIEF DESCRIPTION OF THE DRAWINGS

These features and advantages of the invention will appear more clearly upon reading the following description, given solely as a non-limiting example, and made in reference to the attached drawings, in which.

DETAILED DESCRIPTION

In the following of the description, the phrase "substantially equal to" means being equal within 10%, and preferably within 5%.

Figure 1:
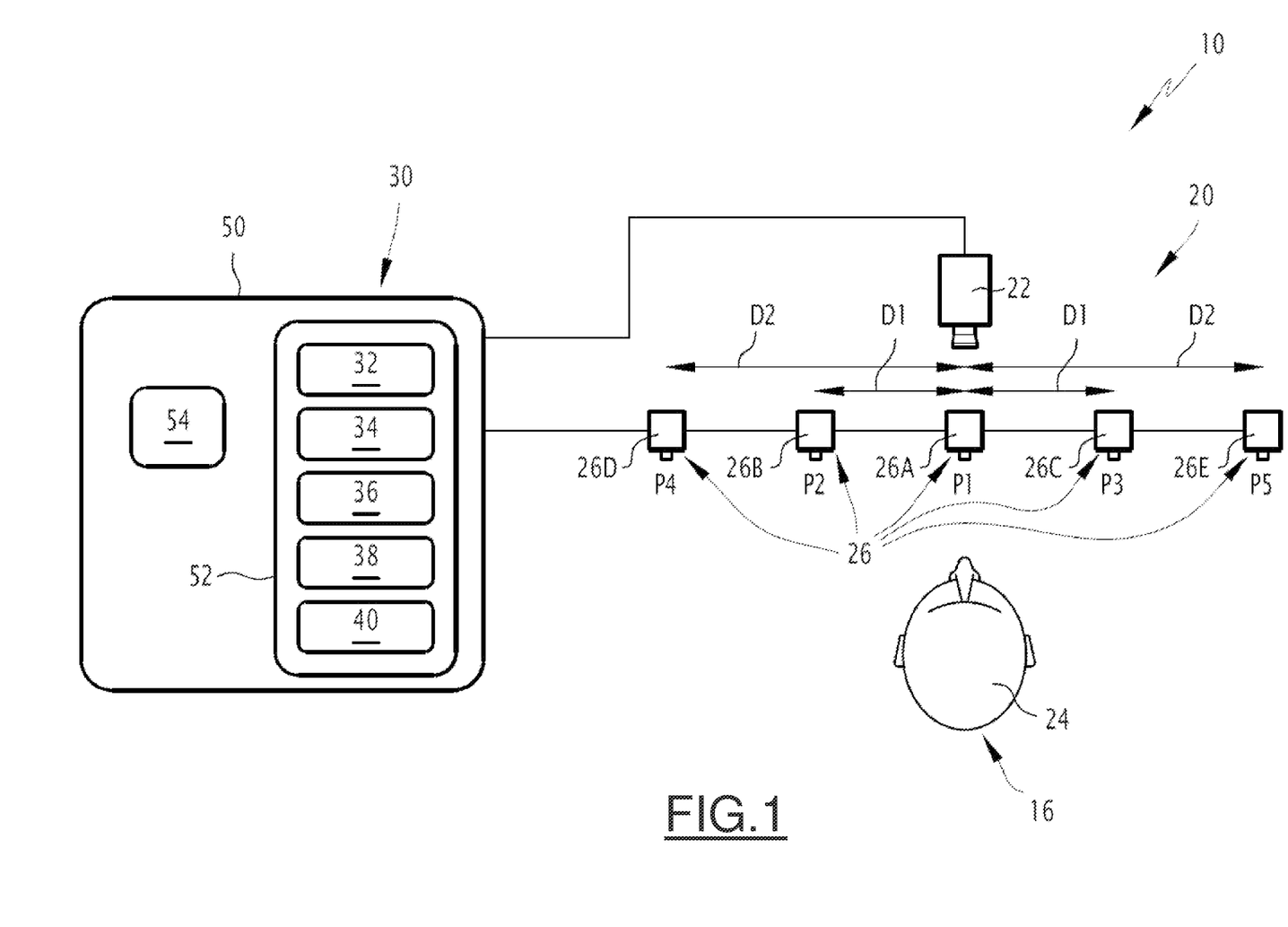
FIG. 1 is a schematic representation of a vehicle, in particular a motor vehicle, comprising an electronic supervision system according to an embodiment of the invention for supervising a driver of the vehicle, the supervision system comprising an image sensor(s) of the driver's head, at least one light source positioned inside a passenger compartment of the vehicle, and an electronic monitoring device for supervising the driver's behavior while driving the vehicle, said device being connected to the image sensor(s) and to the at least one light source.
Figure 2:
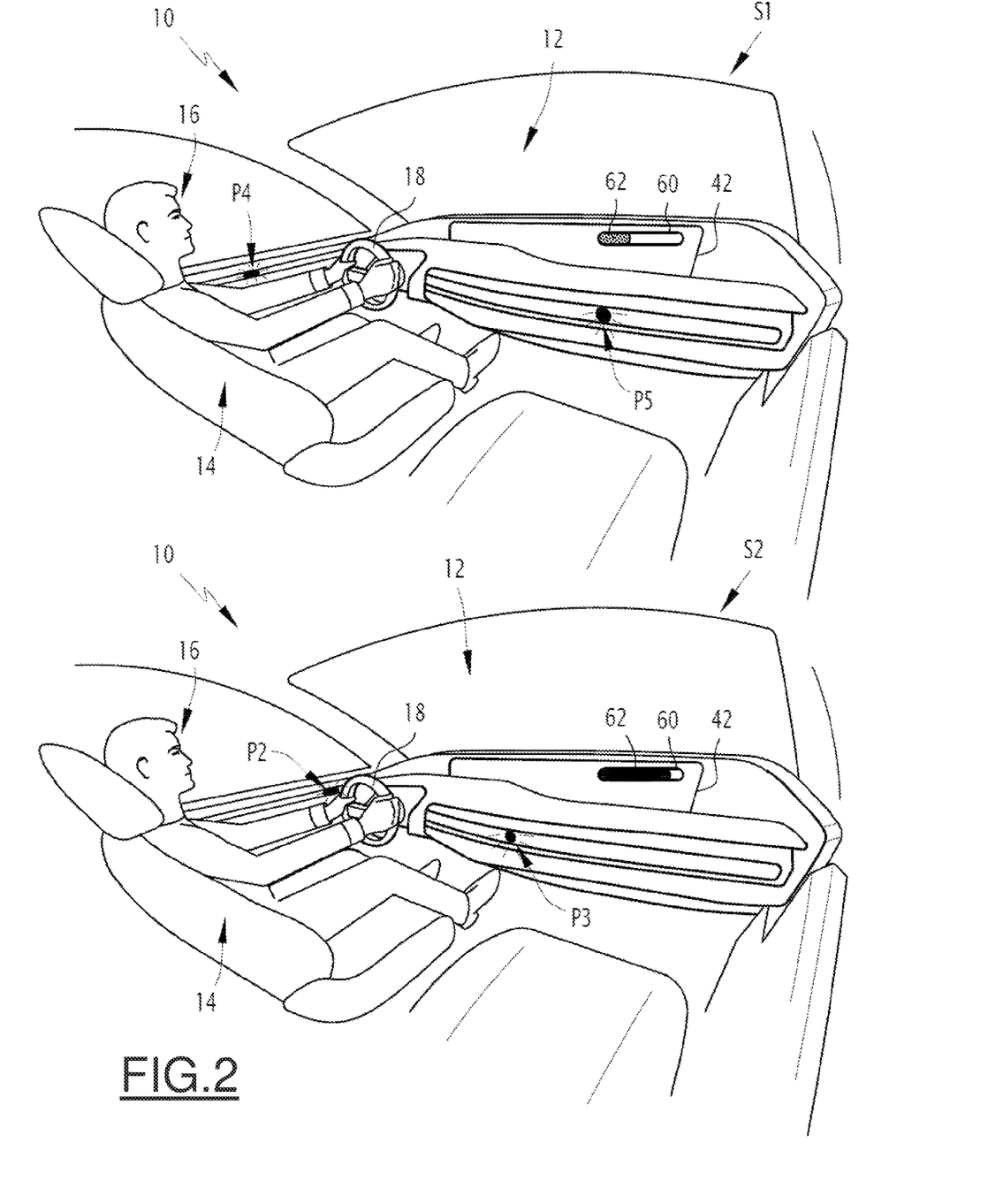
FIG. 2 shows two schematic perspective views of the interior of the vehicle passenger compartment of FIG. 1, a first view corresponding to a first stimulation of the driver, and a second view corresponding to a second stimulation of the driver, the second stimulation being activated if the driver's reaction to the first stimulation was evaluated as insufficient, and the second stimulation having a higher stimulation level than the first stimulation.

In FIGS. 1 and 2, a vehicle 10 comprises a passenger compartment 12; and within the passenger compartment 12, a seat 14 for a driver 16, and a steering wheel 18 for driving the vehicle, as is known per se.

According to the invention, the vehicle 10 further comprises an electronic system 20 for supervising the driver 16 of the vehicle, the supervision system 20 being adapted to be carried on board the vehicle 10.

The skilled person will understand that the vehicle 10 is broadly understood to be a vehicle that allows a driver, also called a pilot, and additionally one or more passengers, to travel. The vehicle 10 is then typically selected from the group consisting of: a motor vehicle, such as a car, bus or truck; a rail vehicle, such as a train or tram; a marine vehicle, such as a ship; and an aviation vehicle, such as an aircraft.

The electronic supervision system 20 comprises an image sensor(s) 22 configured to acquire at least one image of the head 24 of the driver 16, at least one light source 26 configured to be positioned within the passenger compartment 12 of the vehicle, and an electronic device 30 for monitoring the behavior of the driver while driving the vehicle 10, the monitoring device 30 being connected to the image sensor(s) 22 and the at least one light source 26.

The supervision system 20 preferably comprises a plurality of light sources 26 at separate positions within the passenger compartment 12.

In the example of FIG. 1, the supervision system 20 comprises five light sources 26, namely a first light source 26A, a second light source 26B, a third light source 26C, a fourth light source 26D and a fifth light source 26E.

The skilled person will understand that light source, designated by the general reference 26, means any source capable of emitting a luminous flux, such as a bulb, one or more light-emitting diodes, also called LEDs, all or part of a display screen, etc.

The image sensor(s) 22 is known per se and is configured to acquire at least one image of the head 24 of the driver 16, in particular to enable tracking of the movement of the head 24 and eyes of the driver 16. The image sensor(s) 22 is typically positioned opposite the seat 14, and is preferably positioned in line with the steering wheel 18 and the seat 14.

The first light source 26A is positioned at a first position P1, for example close to the steering wheel 18, facing the driver 16 when he is sitting on the seat 14.

The second light source 26B is positioned at a second position P2, and the third light source 26C is positioned at a third position P3, the second and third positions P2, P3 preferably being located on either side of the first position P1, and for example on either side of the steering wheel 18. The second and third positions P2, P3 are preferably also arranged substantially symmetrically with respect to the first position P1. In other words, the second and third positions P2, P3 are for example each separated from the first position P1 by a distance substantially equal to a first distance D1.

Likewise, the fourth light source 26D is positioned at a fourth position P4, and the fifth light source 26E is positioned at a fifth position P5, the fourth and fifth positions P4, P5 preferably being located on either side of the first position P1, and for example on either side of the steering wheel 18. The fourth and fifth light sources 26D, 26E are preferably positioned substantially symmetrically with respect to the first light source 26A, and the fourth and fifth positions P4, P5 are then substantially symmetric with respect to the first position P1. The fourth and fifth positions P4, P5 are each separated from the first position P1 by a distance substantially equal to a second distance D2.

As an optional supplement, the fourth and fifth light sources 26D, 26E are further away from the first light source 26A than the second and third light sources 26B, 26C. In other words, according to this optional supplement, the second distance D2 is greater than the first distance D1. The second distance D2 is, for example, approximately twice the first distance D1.

In addition or alternatively to this distinction between light sources 26 by their respective positions, the light sources 26 are configured to emit respective light signals with distinct colors, and for example with a color varying from one respective light signal to the next, each light signal emitted by a respective light source 26 then having a respective color.

In addition or alternatively, the light sources 26 are configured to emit light signals with different brightnesses, i.e. with a light signal brightness varying from one light source 26 to another.

In addition or alternatively, the light sources 26 are configured to emit light signals with different frequencies, i.e. with a light signal frequency varying from one light source 26 to another.

Each light source 26 is configured to emit a light signal comprising one or more successive light pulses, each with a predefined duration. If the light signal comprises several light pulses, each light pulse preferably has the same predefined duration.

The skilled person will then understand that when the light signal comprises a single light pulse, a variation in the frequency of the light signal, from one light source 26 to another, corresponds to a variation in the duration of the light pulse, from one light source 26 to another.

When the light signal comprises a series of light pulses, these light pulses preferably being emitted periodically, a variation in the frequency of the light signal from one light source 26 to another then typically corresponds to a variation in the period of emission of these light pulses, i.e. to a variation in the duration between two successive light pulses. Alternatively, in relation to the series of light pulses for each respective light signal, a variation in the frequency of the light signal from one light source 26 to another corresponds to a variation in the duration of each of the light pulses.

The electronic monitoring device 30, visible in FIG. 1, is configured to monitor the behavior of the driver 16 while driving the vehicle 10. The electronic monitoring device 30 comprises a module 32 for detecting abnormal behavior of the driver 16 from at least one image of the driver's head 24, a module 34 for stimulating the driver 16 following the detection of said abnormal behavior and a module 36 for evaluating a reaction of the driver 16 following said stimulation.

As an optional supplement, the electronic monitoring device 30 further comprises a module 38 for generating an alert if N insufficient reactions of the driver 16 are successively evaluated.

As a further optional supplement, the electronic monitoring device 30 further comprises a module 40 for displaying information on a display screen 42 arranged inside the passenger compartment 12, as shown in FIG. 2, in particular information relating to the behavior of the driver 16 and/or his reaction to a stimulation.

In the example of FIG. 1, the electronic monitoring device 30 comprises an information processing unit 50 formed for example by a memory 52 and a processor 54 associated with the memory 52.

In the example of FIG. 1, the detection module 32, the stimulation module 34 and the evaluation module 36, and in the optional supplement the generation module 38 and the display module 40, are each in the form of software, or a software brick, which can be executed by the processor 54. The memory 52 of the monitoring device 30 is then able to store software for detecting abnormal behavior of the driver 16, software for stimulating the driver 16 following the detection of said abnormal behavior and software for evaluating a reaction of the driver 16 following said stimulation. As an optional supplement, the memory 52 of the monitoring device 30 is adapted to store software for generating an alert if N insufficient reactions of the driver 16 are successively evaluated, and software for displaying information on the display screen 42. The processor 54 is then able to execute each one of the detection software, the stimulation software and the evaluation software, and optionally the generation software and the display software.

In a variant not shown, the detection module 32, the stimulation module 34 and the evaluation module 36, and in the optional supplement the generation module 38 and the display module 40, are each in the form of a programmable logical component, such as a FPGA (Field-Programmable Gate Array), or as a dedicated integrated circuit, such as an ASIC (Application-Specific Integrated Circuit).

When the monitoring device 30 is in the form of one or more software, that is to say in the form of a computer program, also called a computer program product, it is also capable of being stored on a computer-readable medium, not shown. The computer-readable medium is, for example, a medium that can store electronic instructions and be coupled with a bus from a computer system. For example, the readable medium is an optical disk, magneto-optical disk, ROM memory, RAM memory, any type of non-volatile memory (for example EPROM, EEPROM, FLASH, NVRAM), magnetic card or optical card. The readable medium in such a case stores a computer program comprising software instructions.

The detection module 32 configured to detect abnormal behavior of the driver 16, from at least one image of said driver's head 24 acquired by the image sensor(s) 22.

The detection module 32 is for example configured to detect an absence of movement of the eyes of the driver 16 for a duration greater than a first predefined threshold, said absence of movement being the abnormal behavior to be detected.

As an optional supplement, the detection module 32 is for example configured to detect an absence of movement of both the head 24 and the eyes of the driver 16 for a duration greater than a first predefined threshold, the abnormal behavior then corresponding to said absence of movement of the head 24 and the eyes of the driver 16.

The detection module 32 is for example configured to detect said lack of movement via an image processing algorithm applied to the image(s) of the driver's head 24 acquired by the image sensor 22. The image processing algorithm is known per se.

The first predefined threshold is a predefined time duration, and is for example between 5 and 15 seconds, preferably substantially equal to 10 seconds.

The stimulation module 34 configured to, following the detection of said abnormal behavior of the driver 16, command an emission of at least one light signal by switching on at least one respective light source 26 according to a predefined initial stimulation level.

As an optional supplement, and if the supervision system 20 comprises multiple light sources 26, the stimulation module 34 is configured to command, following the detection of said abnormal behavior of the driver 16, the emission of several light signals at the same time, by switching on M light sources 26 located at distinct positions inside the passenger compartment 12. The M light sources that can be switched on at the same time, following the corresponding command from the stimulation module 34, are preferably arranged on either side of the steering wheel 18.

According to this optional supplement, the number M of light sources 26 switched on at the same time, i.e. the number M of light signals emitted at the same time following the corresponding command from the stimulation module 34, is preferably equal to 2. The M light sources 26 that are switched on at the same time are preferably also arranged substantially symmetrically in relation to the steering wheel 18.

According to this optional supplement, the distance between the two light sources 26 switched on at the same time is decreasing from one light signal emission to the next, i.e. from one light stimulation to the next, which then also allows an estimation of a value of the useful field of view of the driver 16, or U FOV for short. The value of the useful field of view of the driver 16 then depends on the positions of the light signals that caused the driver 16 to react sufficiently, and in particular on the distance between the two positions of the two light sources 26 switched on at the same time. The value of the useful field of view of the driver 16 is typically proportional to this distance between the two positions of the two light sources 26 switched on at the same time, which caused a sufficient reaction from the driver 16. The decrease, from one light stimulation to the next, of the distance between the two light sources 26 switched on at the same time then makes it possible to progressively refine, in particular to reduce, the estimate of the value of the useful field of view of the driver 16 until a sufficient reaction of the driver 16 is obtained, and to then estimate the value of the useful field of view of the driver 16 as a function of said distance between the two positions that caused a sufficient reaction from the driver 16.

According to this optional supplement, by way of example, the stimulation module 34 is then configured to control the emission of several light signals at the same time via the lighting of the fourth and fifth light sources 26D, 26E located on either side of the steering wheel 18, at the fourth and fifth positions P4, P5, each substantially at the second distance D2 away from the first light source 26A located at the first position P1, which is close to and facing the position of the steering wheel 18 inside the passenger compartment 12; or by switching on the second and third light sources 26B, 26C located on either side of the steering wheel 18, at the second and third positions P2, P3, each substantially at the first distance D1 away from the first light source 26A.

The evaluation module 36 is configured to evaluate a reaction of the driver 16 from at least one image of the driver's head 24 following the emission of the at least one light signal commanded by the stimulation module 34, the at least one image of the head 24 being acquired by the image sensor 22.

The evaluation module 36 is for example configured to evaluate the driver's 16 reaction based on a reaction time of the driver 16 since the at least one light signal was emitted. The evaluation module 36 is then typically configured to evaluate that the reaction of the driver 16 is insufficient if the reaction time of the driver 16 since said transmission is greater than a second predefined threshold. The second threshold is a time duration, and the value of the second threshold is for example between 2 and 3 seconds, and preferably substantially equal to 2.5 seconds, i.e. 2,500 ms.

As an optional supplement, the evaluation module 36 is further configured to estimate a distraction level, such as a level of cognitive distraction of the driver 16, based on the reaction time of the driver 16 since the emission of the at least one light signal. According to this optional supplement, for a given level of stimulation, the higher the reaction time, the higher the estimated distraction level.

As a further optional supplement, the stimulation module 34 is configured, following the evaluation of an insufficient reaction of the driver 16 by the evaluation module 36, to command a new emission of at least one light signal with a next stimulation level, distinct from the initial stimulation level. The next stimulation level is, for example, higher than the initial stimulation level.

As a further optional supplement, the stimulation module 34 is configured to command said new emission of at least one light signal only after the expiry of a predefined duration since the previous emission of at least one light signal. Said predefined time is typically greater than the second predefined threshold, and is for example substantially equal to 3 seconds.

According to this optional supplement, each stimulation level is dependent on at least one of a position of the respective light signal, a color of the respective light signal, a brightness of the respective light signal or a frequency of the respective light signal, or dependent on a combination of said parameters.

A higher stimulation level typically corresponds to a position of the light signal closer to the driver 16, or a darker color of the light signal, or a higher brightness of the light signal, or a higher frequency of the light signal, or a combination of the above.

The stimulation module 34 is then, for example, configured to command the respective emission of at least one light signal according to a respective stimulation level among P stimulation levels, P preferably being greater than or equal to 3, and even more preferably equal to 3.

The stimulation module 34 is preferably configured to command each emission of at least one light signal with an increasing stimulation level from one emission to the next.

By way of example, the stimulation module 34 is configured to command a first emission of light signal(s) with a first stimulation level; then configured to—in the event of evaluation of an insufficient reaction of the driver 16 following this first emission—command a second emission of light signal(s) according to a second stimulation level higher than the first stimulation level; and finally configured to—in the event of evaluation of an insufficient reaction of the driver 16 following the second emission—command a third emission of light signal(s) with a third stimulation level higher than the second stimulation level.

As an optional supplement, the generating module 38 is configured to generate an alert if N insufficient reactions of the driver 16 are successively evaluated by the evaluation module 36, where N is a predefined integer. The number N is for example greater than or equal to 3, and preferably equal to 3.

The number N of insufficient reactions leading to the generating of an alert is preferably equal to the number P of distinct stimulation levels.

As an optional supplement, the display module 40 is configured to display information on the display screen 42 arranged opposite the driver 16. In particular, the display module 40 is configured to display on the screen 42 information relating to the behavior of the driver 16, such as the distraction level of the driver 16 estimated by the evaluation module 36.

According to this optional supplement, the distraction level is for example represented as a scale 60 and a cursor 62 associated with that scale 60, as shown in FIG. 2. In the example of FIG. 2, a first situation S1 corresponds to a first schematic perspective view shown in the upper part of FIG. 2, and illustrates a medium or even low distraction level, the cursor 62 representing the distraction level being in a position less than half of the scale 60, the cursor 62 then further showing a greyed-out fill, typically corresponding to a green color of a normal situation. In this example of FIG. 2, a second situation S2 corresponding to a second schematic perspective view shown in the lower part of FIG. 2, illustrates, in turn, a high distraction level of the driver 16, the cursor 62 representing the distraction level of the second situation S2 being then close to the maximum value of the scale 60, the cursor 62 then showing in addition a dark fill, typically corresponding to a red color of an abnormal situation.

Figure 3:
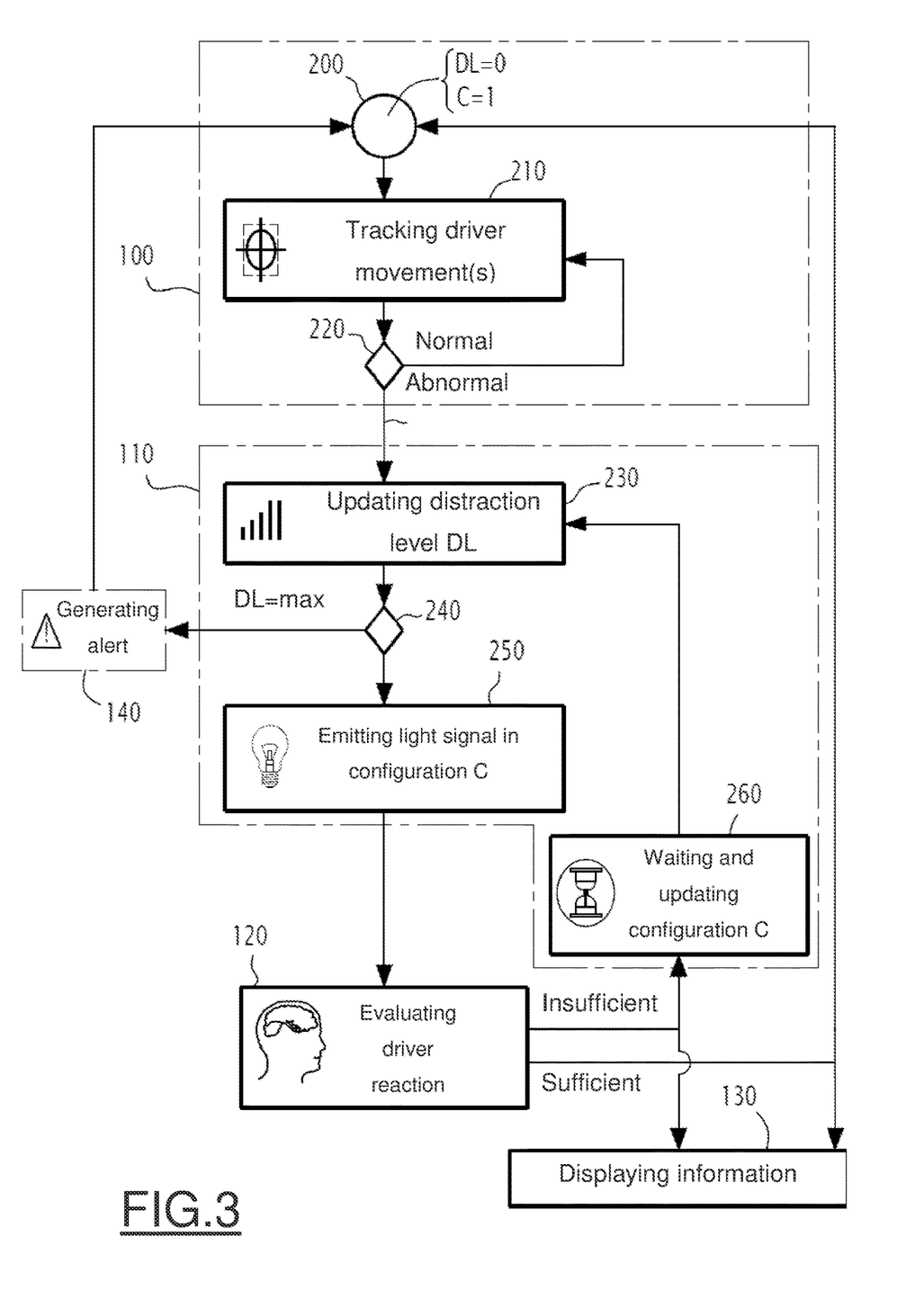
FIG. 3 is a flowchart of a monitoring method according to the invention for monitoring the behavior of the vehicle's driver, the method being implemented by the electronic monitoring device of FIG. 1.

The operation of the supervision system 20, and in particular of the monitoring device 30, according to the invention will now be described with reference to FIG. 3 showing a flow chart of the monitoring method, according to the invention, for monitoring the behavior of the driver 16 while driving the vehicle 10.

In an initial step 100, the monitoring device 20 begins, via its detection module 32, to monitor the behavior of the driver 16, based on image(s) of the driver's head 24 acquired by the image sensor(s) 22, to detect any abnormal behavior of the driver.

As long as the behavior of the driver 16 is considered normal, the monitoring device 30 remains in this initial stage 100.

If, in this initial detection step 100, the monitoring device 30 detects, via its detection module 32, an abnormal behavior of the driver 16, then the monitoring device proceeds to the next step 110 in which its stimulation module 34 stimulates the driver 16 by commanding the emission of at least one light signal, by switching on at least one respective light source 26 according to a predefined initial stimulation level.

In the next step 120, the monitoring device 30 evaluates, via its evaluation module 36, a reaction of the driver 16 following the stimulation carried out in the preceding stimulation step 110, and from at least one image of the driver's head 24, acquired by the image sensor(s) 22 following the emission of the at least one light signal.

As an optional supplement, during the evaluation step 120, the evaluation module 36 estimates the distraction level, such as the level of cognitive distraction of the driver 16, based on the reaction time of the driver 16 since the emission of the at least one light signal. For a given level of stimulation, the higher the reaction time, the higher the estimated distraction level.

At the end of the evaluation step 120, if the reaction of the driver 16 is evaluated as sufficient, then the monitoring device 30 returns to the initial step 100 to resume monitoring the behavior of the driver 16.

Alternatively, if the response of the driver 16 is instead evaluated as insufficient, then the monitoring device 30 returns to the stimulation step 110 to re-stimulate the driver 16 with a next level of stimulation distinct from that of the previous stimulation, the next level of stimulation being, for example, higher than the initial level of stimulation.

As an optional supplement, the monitoring device 30 displays, via its display module 40 and in a step 130, on the display screen 42 arranged opposite the driver 16, information relating to the behavior of the driver 16, such as the distraction level of the driver 16 optionally additionally estimated in the evaluation step 120. In the example of FIG. 2, the distraction level is represented via the cursor 62 associated with the scale 60.

At the end of this new stimulation step 110, the monitoring device 30 goes again to the evaluation step 120, to re-evaluate the reaction of the driver 16 following this new stimulation.

At the end of this further iteration of the evaluation step 120 and similarly to what was performed at the end of the first iteration of the evaluation step 120, if the evaluation of the driver's reaction to the new stimulation is evaluated as sufficient, then the monitoring device 30 returns to the initial step 100, and otherwise it returns to the stimulation step 110 to perform a new stimulation of the driver 16 with a stimulation level distinct from that of the previous stimulation, for example higher than that of the previous stimulation.

As an optional supplement, if at the end of N iterations of the stimulation steps 110 and evaluation steps 120, N insufficient reactions of the driver 16 have been evaluated successively, N being for example greater than or equal to 3, and preferably equal to 3, then the monitoring device 30 generates, in step 140 and via its generating module 38, an alert, such as an audible alert, to make the driver 16 react further and become aware that his distraction level is too high and that he must then concentrate again on driving the vehicle 10, to avoid a driving accident with said vehicle 10.

In FIG. 3, the detection step 100 comprises an initial sub-step 200 during which two variables are initialized, namely a first variable denoted DL associated with the distraction level, the value of which is set to zero during this initial sub-step 200, and a second variable denoted C corresponding to a light signal emission configuration, the value of which is initialized to 1 during this initial sub-step 200.

The detection step 100 comprises, following this initial sub-step 200, a sub-step 210 during which the detection module 32 carries out a tracking of movement(s) of the driver 16, in particular a tracking of movement(s) of the head 24 and of the eyes of the driver 16, based on image(s) of the head 24 acquired by the image sensor 22.

Periodically at the end of the monitoring substep 210, the detection module 32 determines whether the driver's behavior is normal or abnormal, where abnormal behavior is defined as no movement of the driver's eyes 16 or no movement of the driver's head and eyes 16 for a duration greater than the first predefined threshold. This determination is made in a test sub-step 220.

At the end of the test sub-step 220, the detection module 32 returns to the monitoring sub-step 210 if the detection module 32 has determined that the behavior of the driver 16 was normal, and proceeds to a next sub-step 230 in case of detection of abnormal behavior of the driver 16, i.e. absence of movement as defined above, based on image(s) of the head 24 showing immobilization of the head 24 and eyes of the driver 16.

The stimulation step 110 then comprises, for example, a distraction level update sub-step 230 in which the stimulation module 34 updates the distraction level of the driver 16. This update consists, for example, of incrementing the first variable DL associated with the distraction level by one unit, doing so at each iteration of this update sub-step 230, except for the first iteration of this sub-step 230 when no light signal(s) has yet been emitted.

Following this update sub-step 230, the stimulation step 110 comprises a test sub-step 240 in which the stimulation module 34 determines whether the value of the distraction level has reached a predefined maximum or not. If the value of the first variable DL associated with the distraction level is less than a maximum value MAX, then the stimulation module 34 proceeds to a sub-step 250 in which it commands the emission of at least one light signal according to the configuration associated with the second variable C, and via the switching on of at least one respective light source 26. The light signal(s) emission configuration corresponds to a respective stimulation level, and the initial value 1 of the second variable C associated with said emission configuration then typically corresponds to the first stimulation level.

At the end of this transmission substep 250 implemented by the stimulation module 34, the monitoring device 30 proceeds to the evaluation step 120 implemented by the evaluation module 36 and described above.

If the reaction of the driver 16, evaluated in the evaluation step 120 by the evaluation module 36, is insufficient, then the monitoring device 30 proceeds to a sub-step 260 in which the stimulation module 34 waits for the expiry of the predefined duration since the previous light signal emission, this predefined duration being typically equal to 3 seconds.

During this sub-step 260, the stimulation module 34 further updates the second variable C associated with the light signal emission configuration, this update corresponding, for example, to incrementing the second variable C by one unit, so that the next light signal emission is carried out according to a configuration having a value incremented by one unit, and then corresponding to a stimulation level higher than that used for the previous light signal emission.

At the end of the wait and update substep 260, the stimulation module 34 returns to the substep 230 of updating the first variable DL associated with the distraction level. At the end of this update sub-step 230, the stimulation module 34 again tests the value of the first variable DL during the test sub-step 240, and determines whether it is equal to the maximum value MAX, and if so proceeds to the alert generation step 240, implemented by the generation module 38 and described previously.

If during the test substep 240, the value of the first variable DL is less than the maximum value MAX, then the stimulation module 34 returns to the substep 250 to carry out a new light signal emission according to a configuration corresponding to the second variable C incremented by one unit, i.e. with a stimulation level higher than that of the previous light signal emission.

This increment in configuration, or stimulation level, corresponds, for example, to a position of the emitted light signal closer to the driver 16, i.e. to the switching on of a light source 26 positioned closer to the driver 16 than the light source(s) 26 that had been switched on during the previous light signal emission.

Alternatively or additionally, this increment in the configuration or stimulation level corresponds to a darker color of the emitted light signal, or a higher brightness of the emitted light signal, or a higher frequency of the emitted light signal, or a combination of the above changes.

The skilled person will then observe that in the example of FIG. 3, the stimulation step 110 comprises the update 230, test 240, emission 250, and wait and update 260 sub-steps.

For example, the number P of stimulation levels is assumed to be 3, and the number N of light sources 26 is assumed to be 5, as in the example of FIG. 1 with the first, second, third, fourth, and fifth light sources 26A, 26B, 26C, 26D, and 26E positioned at the first, second, third, fourth, and fifth positions P1, P2, P3, P4, and P5 respectively.

According to a first scenario, during the first iteration of the stimulation step 110, the stimulation module 34 commands the emission of light signals at the fourth and fifth positions P4, P5, by switching on the fourth and fifth light sources 26D, 26E, typically during the first iteration of the sub-step 250.

In the first iteration of the evaluation step 120, the monitoring device 30 then evaluates the reaction of the driver 16 via its evaluation module 36. If the evaluation module 36 determines that the driver 16 has perceived the emission of the light signals at the fourth and fifth positions P4, P5 with a reaction time of less than the second predefined threshold associated with this first stimulation, such as 2.5 seconds, then the evaluation module 36 evaluates the reaction of the driver 16 as sufficient. The evaluation module 36 further estimates, as an optional supplement, that the value of the distraction level is zero, corresponding to an absence of distraction risk.

If, on the other hand, the evaluation module 36 determines that the driver 16 has not perceived the emission of light signals at the fourth and fifth positions P4, P5 with a reaction time lower than the second predefined threshold, then it evaluates the reaction of the driver 16 as insufficient, and returns to the stimulation step 110 so that the configuration C is incremented by one unit, and that according to this first scenario, the stimulation module 34 commands the emission of light signals at the second and third positions P2, P3 by switching on the corresponding second and third light sources 26B, 26C.

After this new, second iteration of the stimulation step 110, the monitoring device 30 again proceeds to the evaluation step 120, in which the evaluation module 36 determines whether the driver 16 has perceived the emission of the light signals at the second and third positions P2, P3 with a reaction time of less than the second predefined threshold, the value of which is, for example, equal to 2.5 seconds for this second stimulation. If the driver 16 has reacted with a reaction time of less than this second predefined threshold, then the evaluation module 36 evaluates in the evaluation step 120 that the reaction of the driver 16 is sufficient.

Furthermore, as an optional supplement, the evaluation module 36 estimates the value of the distraction level according to the value of the reaction time since the second light stimulation, i.e. since the emission of the light signals at the second and third positions P2, P3. If the reaction time of the driver 16 is less than an intermediate threshold, e.g. 1.5 seconds, then the evaluation module 36 estimates the value of the distraction level to be 1, corresponding to a medium risk of distraction; and if the reaction time of the driver 16 is between the intermediate threshold and the second predefined threshold, e.g. between 1.5 seconds and 2.5 seconds, then the evaluation module 36 estimates the value of the distraction level to be 2, corresponding to a high risk of distraction.

If, in the evaluation step 120, the reaction of the driver 16 is evaluated as sufficient, then the monitoring device 30 returns to the initial detection step 100 with an estimated distraction level of 1 or 2 depending on the value of the reaction time of the driver 16.

If, on the contrary, the reaction of the driver 16 is evaluated as insufficient in the evaluation step 120, i.e. if the driver 16 has not perceived the emission of the light signals at the second and third positions P2, P3 with a reaction time lower than the second predefined threshold, then the monitoring device 30 returns to the stimulation step 110 to carry out a new stimulation of the driver 16 with a stimulation level distinct from that of the previous stimulation, for example higher than that of the previous stimulation. The updating of the configuration carried out during sub-step 260 then corresponds to a change in the emission position of the light signal, and during this third iteration of the stimulation step 110, in particular during the third iteration of the emission sub-step 250, the stimulation module 34 commands the emission of the light signal at the first position P1, by switching on the first light source 26A.

The monitoring device 30 then proceeds again to the evaluation step 120, to perform a third iteration thereof, and to determine in particular whether the driver 16 has perceived the emission of the light signal at the first position P1 with a reaction time less than the second predefined threshold whose value for this third iteration of the evaluation step 120 is less than that used for the two previous iterations of the evaluation step 120, the second predefined threshold being for example substantially equal to 500 ms for this third iteration of the evaluation step 120.

In other words, if the evaluation module 36 determines that the driver 16 has not perceived the emission of the light signal at the first position P1 with a reaction time of less than 0.5 seconds, then it evaluates the reaction of the driver 16 as insufficient. As an optional supplement, the evaluation module 36 estimates the value of the distraction level to be 3, corresponding to a very high risk of distraction. In this example, the value 3 corresponds to the maximum value MAX for the distraction level, and in the next test substep 240, the stimulation module 34 then determines that the first variable DL associated with the distraction level has reached the maximum value MAX, and then proceeds to the optional step 140 of generating an alert, such as an audible alert.

According to a second scenario, with the example of five light sources 26A to 26E, the first stimulation configuration still corresponds to the emission of the light signals at the fourth and fifth positions P4, P5 by switching on the fourth and fifth light sources 26D, 26E, this time also with a first color of the light signal emitted for this first stimulation.

The second stimulation configuration implemented if the reaction of the driver 16 has been evaluated as insufficient following the first stimulation, corresponds in this second scenario to the emission of light signals at the second and third positions P2, P3 by switching on the second and third light sources 26B, 26C, with in addition a color of the light signals emitted at the second and third positions P2, P3 which is darker than that of the light signals emitted during the first stimulation at the fourth and fifth positions P4, P5.

According to this second scenario, if the reaction of the driver 16 is again evaluated as insufficient following this second stimulation, then the stimulation module 34 moves to the third stimulation configuration, in which the commanded light signal emission is an emission of the light signal at the first position P1 via the switching on of the first light source 26A, with furthermore a darker color at the first position P1 than that of the light signals previously emitted for the second stimulation at the second and third positions P2, P3.

In other words, according to this second scenario, the different stimulation levels correspond to positions of the light signals closer to the driver 16 as the stimulation level increases, and also to darker colors of the emitted light signal(s) as the stimulation level increases.

The skilled person will observe that under this second scenario, the estimation of the different values of the distraction level is similar to that performed under the first scenario.

According to a third scenario, the stimulation levels correspond both to positions of the light signals that are closer to the driver 16 as the stimulation level increases, and further to a higher brightness of the light signal(s) emitted at the respective positions as the stimulation level increases. During a possible second iteration of the stimulation step 110, the stimulation module 34 then commands the emission of the light signals at the second and third positions P2, P3 with a greater brightness than that of the signals emitted during the first iteration of the stimulation step 110 for the light signals at the fourth and fifth positions P4, P5. Similarly, during a possible third iteration of the stimulation step 110, the stimulation module 34 commands the emission of the light signal at the first position P1 with a greater light signal brightness than that of the signals emitted during the second iteration of the stimulation step 110 for the light signals at the second and third positions P2, P3.

The skilled person will then observe that under this third scenario, the evaluation module 36 evaluates the different values of the distraction level in a similar way to the estimation of the values of the distraction level according to the first scenario, or even under the second scenario.

In addition, other stimulation scenarios are possible, for example by combining different emission positions of the light signals, as described above for the first, second and third scenarios, this time with an increase in the frequency of the light signal from one stimulation level to another.

Alternatively, when the supervision system 20 comprises a single light source 26, the skilled person will understand that the variation of the stimulation level is likely to be implemented by varying the color of the light signal from one stimulation level to another, with typically a darker color of the light signal for a higher stimulation level; or by varying the brightness of the light signal from one stimulation level to another, typically with a higher brightness of the light signal for a higher stimulation level; or by varying the frequency of the light signal from one stimulation level to another, typically with a higher frequency of the light signal for a higher stimulation level.

The skilled person will further observe that in the example of FIG. 2, the first situation S1 corresponds to the first stimulation level, with the emission of the light signals at the fourth and fifth positions P4, P5, and that the second situation S2 corresponds to the second stimulation level with the emission of the light signals at the second and third positions P2, P3.

Thus, the supervision system 20, and in particular the monitoring device 30, according to the invention makes it possible not only to stimulate a reaction of the driver 16 following a detection of an abnormal behavior of the driver 16, but also to evaluate the reaction of the driver 16 following that stimulation, to carry out a subsequent complementary stimulation action if necessary and/or to help the driver 16 to drive the vehicle 10 by displaying information relating to his evaluated reaction.

This display of information on the display screen 42 then also makes it possible to provide the driver 16 with a driving aid, while helping him to become aware of his distraction level, and encouraging him to be more vigilant if his distraction level presents a significant risk, in particular when it corresponds to a high risk (level 2) or even a very high risk (level 3) of distraction.

As an optional supplement, this evaluation of the driver's reaction 16 can also be used to estimate the distraction level of the driver 16, so that an indication of this can be displayed to the driver 16, so that he or she can be aware of this, and react accordingly, to reduce the risk of a subsequent accident.

The monitoring device 30 according to the invention also makes it possible to estimate a mental load of the driver 16 based on the reaction time of the driver 16 to react to the emission of light signal(s), forming a visual stimulation.

It is thus conceivable that the supervision system 20, and in particular the monitoring device 30, according to the invention make it possible to improve the monitoring of the behavior of the driver 16 when driving the vehicle 10, and thus to reduce the risk of an accident of the vehicle 10.

The invention claimed is:

1. An electronic driver behavior monitor adapted to be carried on board a vehicle and to be connected to an image sensor and to at least one light source positioned within a passenger compartment of the vehicle, the driver behavior monitor being configured to:
   detect abnormal behavior of a driver of the vehicle from at least one image of the driver's head acquired by the image sensor;
   following the detection of said abnormal behavior, command an emission of a plurality of light signals at the same time by switching on a respective number of light sources located at distinct positions inside the passenger compartment according to a predefined initial stimulation level; and following the emission of the plurality of light signals, evaluate a reaction of the driver based on at least one image of the driver's head acquired by the image sensor, wherein a distance between two of the light sources switched on at the same time decreases in a next emission of a plurality of light signals, and wherein a value of a useful field of view of the driver is estimated as a function of the distance between the two light source positions that cause a sufficient reaction from the driver.

2. The monitor according to claim 1, further configured to, following the evaluation of the reaction of the driver as an insufficient reaction, command a new emission of at least one light signal according to a next stimulation level, distinct from the initial stimulation level.

3. The monitor according to claim 2, wherein each stimulation level depends on at least one parameter from the group consisting of: a position of the respective light signal, a color of the respective light signal, a brightness of the respective light signal and a frequency of the respective light signal.

4. The monitor according to claim 1, wherein the light sources are arranged on either side of a driving position of the vehicle.

5. The monitor according to claim 1, wherein the number of light sources is equal to 2.

6. The monitor according to claim 1, wherein the detected abnormal behavior is an absence of eye movement of the driver for a duration greater than a first predefined threshold.

7. The monitor according to claim 1, further configured to evaluate the reaction of the driver as a function of a reaction time of the driver since the emission of the at least one light signal.

8. The monitor according to claim 7, wherein the reaction is evaluated as insufficient if the reaction time of the driver is greater than a second predefined threshold.

9. The monitor according to claim 8, wherein the second threshold is between 2 and 3 seconds.

10. The monitor according to claim 9, wherein the second threshold is equal to 2.5 seconds.

11. The monitor according to claim 1, further configured to estimate a distraction level of the driver based on a reaction time of the driver since the at least one light signal was emitted, and for a given stimulation level, the higher the reaction time, the higher the estimated distraction level.

12. The monitor according to claim 1, further configured to generate an alert if a predefined number of reactions of the driver are successively evaluated as insufficient reactions.

13. The monitor according to claim 12, wherein the predefined number of reactions is greater than or equal to 3.

14. The monitor according to claim 1, further configured to display, on a display screen disposed inside the passenger compartment of the vehicle opposite a seat for the driver, information relating to the behavior of the driver.

15. The monitor according to claim 14, wherein the information is related to the driver's reaction and/or to a distraction level of the driver.

16. The monitor according to claim 1, further configured to command said new emission of at least one light signal only after the expiry of a predefined duration since the previous emission of at least one light signal.

17. An electronic supervision system for supervising a driver of a vehicle, the system being adapted to be carried in the vehicle and comprising:
   an image sensor(s) configured to acquire at least one image of the driver's head;
   at least one light source configured to be positioned within a passenger compartment of the vehicle; and
   the electronic driver behavior monitor according to claim 1 connected to the image sensor(s) and to the at least one light source.

18. A monitoring method for monitoring the behavior of a driver while driving a vehicle, the method being implemented by an electronic driver behavior monitor adapted to be carried on board the vehicle and to be connected to an image sensor of at least one image of the driver's head and to at least one light source positioned within a passenger compartment of the vehicle, the method comprising the following steps:
   detecting abnormal behavior of the drive from at least one image of the driver's head acquired by the image sensor;
   following the detection of said abnormal behavior, commanding an emission of a plurality of light signals at the same time by switching on a respective number of light sources located at distinct positions inside the passenger compartment according to a predefined initial stimulation level;
   following the emission of the plurality of light signals, evaluating a reaction of the driver based on at least one image of the driver's head acquired by the image sensor;
   decreasing a distance between two of the light sources switched on at the same time in a next emission of a plurality of light signals; and
   estimating a value of a useful field of view of the driver as a function of the distance between the two light source positions that causes a sufficient reaction from the driver.

19. A non-transitory, computer-readable medium having stored thereon a computer program comprising software instructions which, when executed by a computer, implement a method according to claim 18.

* * * * *

UNITED STATES PATENT AND TRADEMARK OFFICE
CERTIFICATE OF CORRECTION

| | | |
|---|---|---|
| PATENT NO. | : 11,834,053 B2 | |
| APPLICATION NO. | : 17/711746 | |
| DATED | : December 5, 2023 | |
| INVENTOR(S) | : Omar Ben Abdelaziz and Nour Besbes | |

It is certified that error appears in the above-identified patent and that said Letters Patent is hereby corrected as shown below:

On the Title Page

In the Title at (54), delete "WITH" and insert --WHILE--

In the Specification

In Column 1, Line 3, delete "WITH" and insert --WHILE--

Signed and Sealed this
Ninth Day of April, 2024

Katherine Kelly Vidal
*Director of the United States Patent and Trademark Office*